United States Patent
Tonomura et al.

(10) Patent No.: US 9,862,812 B2
(45) Date of Patent: Jan. 9, 2018

(54) COMPOSITION CONTAINING NITROGEN-CONTAINING ORGANOXYSILANE COMPOUND AND METHOD FOR MAKING THE SAME

(71) Applicant: Shin-Etsu Chemical Co., Ltd., Tokyo (JP)

(72) Inventors: Yoichi Tonomura, Joetsu (JP); Tohru Kubota, Joetsu (JP); Masato Kawakami, Joetsu (JP); Naoki Yamauchi, Joetsu (JP); Takayuki Honma, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 155 days.

(21) Appl. No.: 14/546,402

(22) Filed: Nov. 18, 2014

(65) Prior Publication Data

US 2015/0135996 A1 May 21, 2015

(30) Foreign Application Priority Data

Nov. 20, 2013 (JP) .................................. 2013-239681

(51) Int. Cl.
*C07F 7/18* (2006.01)
*C08K 5/544* (2006.01)

(52) U.S. Cl.
CPC .............. *C08K 5/544* (2013.01); *C07F 7/184* (2013.01); *C07F 7/1836* (2013.01); *C07F 7/1844* (2013.01); *C07F 7/1852* (2013.01); *C07F 7/1876* (2013.01)

(58) Field of Classification Search
CPC ...... C07F 7/1836; C07F 7/184; C07F 7/1852; C07F 7/1844
See application file for complete search history.

(56) References Cited

U.S. PATENT DOCUMENTS

2006/0241294 A1* 10/2006 Tonomura ............... C07F 7/184
544/229

FOREIGN PATENT DOCUMENTS

| EP | 0362509 A1 | 4/1990 |
| EP | 1714968 A1 | 10/2006 |
| JP | 2008-143855 A | 6/2008 |
| JP | 2013-60376 A | 4/2013 |

OTHER PUBLICATIONS

Sabourault, Nicolas et al., "Platinum Oxide (PtO(2)): A Potent Hydrosilylation Catalyst", Organic Letters, American Chemical Society, US, Jun. 27, 2002, vol. 4. No. 13, pp. 2117-2119, in Extended European Search dated Mar. 17, 2015 (3 pages).
Extended European Search Report dated Mar. 17, 2015, issued in corresponding EP Patent Application No. 14193598.1 (6 pages).
Kashutina, E., A., at al., "Synthesis of Some Organofunctional Silanes and the Modification of Silica Surfaces With Them", Zhurnal Obschei Khimii, Mar. 1984, vol. 54, No. 3, pp. 657-662, in Specification, with English translation.

* cited by examiner

*Primary Examiner* — David M Brunsman
(74) *Attorney, Agent, or Firm* — Westerman, Hattori, Daniels & Adrian, LLP

(57) ABSTRACT

A composition consisting essentially of 90-99 parts by weight of a nitrogen-containing organoxysilane compound and 1-10 parts by weight of an isomer affords an appropriate cure behavior and is useful as paint additive, adhesive, silane coupling agent, textile treating agent, and surface treating agent.

3 Claims, No Drawings

COMPOSITION CONTAINING NITROGEN-CONTAINING ORGANOXYSILANE COMPOUND AND METHOD FOR MAKING THE SAME

CROSS-REFERENCE TO RELATED APPLICATION

This non-provisional application claims priority under 35 U.S.C. §119(a) on Patent Application No. 2013-239681 filed in Japan on Nov. 20, 2013, the entire contents of which are hereby incorporated by reference.

TECHNICAL FIELD

This invention relates to a composition containing nitrogen-containing organoxysilane compound which is useful as paint additive, adhesive, silane coupling agent, textile treating agent, surface treating agent or the like, and a method for preparing the same.

BACKGROUND ART

Amino-bearing silane compounds are known to be useful as paint additive, adhesive, silane coupling agent, textile treating agent, and surface treating agent. Such amino-bearing silane compounds include organoxysilane compounds having a primary amino group such as aminopropyltrimethoxysilane, organoxysilane compounds having a secondary amino group such as N-phenylaminopropyltrimethoxysilane, and organoxysilane compounds having a tertiary amino group such as dimethylaminopropyltrimethoxysilane.

While these amino-bearing organoxysilane compounds are often used in sole compound form, inclusion of an isomer having a branched structure is sometimes preferred. In their application to liquid crystal alignment layer, for example, the presence of an isomer allows for controlled alignment of liquid crystals. In another example, if a compound in single component form is awkward to handle because of a high melting point, the presence of an isomer brings about a lowering of melting point, ensuring ease of handling. Even in these applications, however, there is a risk that if the isomer is present too much, its own effect will be impaired. In this sense, an amino-bearing organoxysilane compound composition containing an appropriate amount of isomer is preferred.

Of the above-mentioned amino-bearing organoxysilane compounds, the organoxysilane compounds having a tertiary amino group such as dimethylaminopropyltrimethoxysilane are useful as a promoter or co-curing agent for acid anhydride, polyamine and polyamide-based epoxy resin curing agents. The organoxysilane compounds having a tertiary amino group also have a possibility that on use of an organoxysilane compound as epoxy resin additive, if it is fully isomer-free, the cure rate will be accelerated; and if it is isomer-rich, the cure rate will be slowed down. In this sense, an organoxysilane compound composition containing an appropriate amount of isomer is preferred.

The method for synthesizing an organoxysilane compound having a tertiary amino group generally relies on hydrosilylation reaction of an unsaturated bond-containing compound having a tertiary amino group and a hydrogenorganoxysilane compound in the presence of a platinum catalyst (see Non-Patent Document 1). Another method for obtaining the organoxysilane compound having a tertiary amino group is by reacting a secondary amine compound with a haloalkylorganoxysilane compound (see Patent Document 1).

CITATION LIST

Patent Document 1: JP-A 2008-143855
Non-Patent Document 1: Zh. Obshch. Khim., 54, 657 (1984)

DISCLOSURE OF INVENTION

The method of Non-Patent Document 1, however, results in a tertiary amino-bearing organoxysilane compound composition containing much isomer because about 30 to 50% by weight of addition isomer forms during hydrosilylation reaction. By contrast, the method of Patent Document 1 fails to obtain a tertiary amino-bearing organoxysilane compound composition containing appropriate isomer because no isomer forms. Besides, the latter method requires cumbersome operation such as filtration because amine hydrochloride forms during reaction. Contamination of the product with amine hydrochloride can degrade the quality of the product. Further, when the secondary amine compound used is gaseous at room temperature like dimethylamine, the reaction must be performed under pressure, which indicates an industrial disadvantage.

An object of the invention is to provide a nitrogen-containing organoxysilane compound composition which affords an appropriate cure behavior when used as paint additive, adhesive, silane coupling agent, textile treating agent, surface treating agent or the like, and a method for preparing the same.

Regarding the synthesis of an organoxysilane compound having a tertiary amino group via hydrosilylation reaction of an unsaturated bond-containing compound having a tertiary amino group and a hydrogenorganoxysilane compound in the presence of a platinum catalyst, the inventors have found that when the reaction is conducted in the presence of an inorganic acid ammonium salt, the amount of addition isomer can be controlled to 1 to 10% by weight, and that a nitrogen-containing organoxysilane compound composition containing such an appropriate amount of addition isomer affords an appropriate cure behavior or addition effect when used as paint additive, adhesive, silane coupling agent, textile treating agent, surface treating agent or the like.

Accordingly, the present invention provides a composition containing nitrogen-containing organoxysilane compound consisting essentially of 90 to 99 parts by weight of a nitrogen-containing organoxysilane compound having the general formula (1) and 1 to 10 parts by weight of a nitrogen-containing organoxysilane compound having the general formula (2).

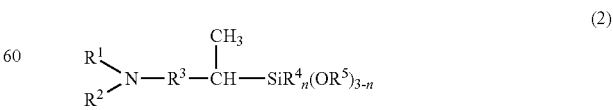

Herein $R^1$ and $R^2$ are each independently a substituted or unsubstituted, monovalent hydrocarbon group of 1 to 20 carbon atoms, or may bond together to form a ring with the nitrogen atom to which they are attached, the ring may contain a heteroatom in addition to the nitrogen atom or have a substituent group, $R^3$ is a divalent hydrocarbon group of 1 to 10 carbon atoms, $R^4$ and $R^5$ are each independently a substituted or unsubstituted, monovalent hydrocarbon group of 1 to 20 carbon atoms, and n is 0, 1 or 2. Preferably, $R^1$ and $R^2$ are methyl and $R^3$ is methylene.

In another aspect, the invention provides a method for preparing the composition containing nitrogen-containing organoxysilane compound defined above, comprising the step of hydrosilylating an unsaturated bond-bearing nitrogen compound having the general formula (3):

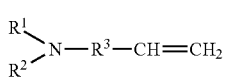
(3)

wherein $R^1$, $R^2$, and $R^3$ are as defined above and a hydrogenorganoxysilane compound having the general formula (4):

$$HSiR^4{}_n(OR^5)_{3-n} \quad (4)$$

wherein $R^4$, $R^5$, and n are as defined above in the presence of an inorganic acid ammonium salt and a platinum catalyst.

ADVANTAGEOUS EFFECT OF INVENTION

The composition containing nitrogen-containing organoxysilane compound affords an appropriate cure behavior or addition effect and is useful as paint additive, adhesive, silane coupling agent, textile treating agent, surface treating agent or the like.

DESCRIPTION OF PREFERRED EMBODIMENTS

The composition containing nitrogen-containing organoxysilane compound of the invention is defined as consisting essentially of:

90 to 99 parts by weight of a nitrogen-containing organoxysilane compound having the general formula (1):

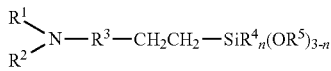
(1)

wherein $R^1$ and $R^2$ are each independently a substituted or unsubstituted, monovalent hydrocarbon group of 1 to 20 carbon atoms, or may bond together to form a ring with the nitrogen atom to which they are attached, $R^3$ is a divalent hydrocarbon group of 1 to 10 carbon atoms, $R^4$ and $R^5$ are each independently a substituted or unsubstituted, monovalent hydrocarbon group of 1 to 20 carbon atoms, n is 0, 1 or 2, and 1 to 10 parts by weight of a nitrogen-containing organoxysilane compound having the general formula (2):

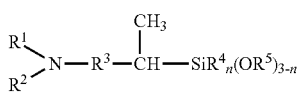
(2)

wherein $R^1$, $R^2$, $R^3$, $R^4$, $R^5$, and n are as defined above.

Herein, $R^1$, $R^2$, $R^4$, and $R^5$ each stand for a substituted or unsubstituted, monovalent hydrocarbon group of 1 to 20 carbon atoms, preferably 1 to 10 carbon atoms, typically selected from straight, branched or cyclic alkyl groups, alkenyl groups, aryl groups, and aralkyl groups. Suitable examples include straight alkyl groups such as methyl, ethyl, propyl, butyl, pentyl, hexyl, heptyl, octyl, decyl, dodecyl, tetradecyl, hexadecyl, octadecyl, and eicosyl; branched alkyl groups such as isopropyl, isobutyl, sec-butyl, tert-butyl, thexyl, and 2-ethylhexyl; cyclic alkyl groups such as cyclopentyl and cyclohexyl; alkenyl groups such as vinyl, allyl and propenyl; aryl groups such as phenyl and tolyl; and aralkyl groups such as benzyl. Inter alia, methyl, ethyl, isopropyl, sec-butyl and tert-butyl are preferred for availability of starting reactants. In the foregoing hydrocarbon groups, one or more or all hydrogen atoms may be substituted by substituent groups, and suitable substituent groups include alkoxy groups such as methoxy, ethoxy and (iso)propoxy, halogen atoms such as fluorine, chlorine, bromine and iodine, cyano groups, amino groups, acyl groups of 2 to 10 carbon atoms, and trialkylsilyl, trialkoxysilyl, dialkylmonoalkoxysilyl, and monoalkyldialkoxysilyl groups in which each of alkyl and alkoxy moieties has 1 to 5 carbon atoms, and a mixture thereof.

Where $R^1$ and $R^2$ bond together to form a ring with the nitrogen atom to which they are attached, $R^1R^2N$— becomes a nitrogen-containing heterocycle. The nitrogen-containing heterocycle may be constructed by a direct link between carbon atom in $R^1$ and carbon atom in $R^2$, or a linkage including at least one heteroatom (e.g., oxygen or nitrogen) interposed between carbon atom in $R^1$ and carbon atom in $R^2$. When $R^1$ and $R^2$ form a ring, the ring preferably contains 3 to 6 carbon atoms.

The nitrogen-containing heterocycle may have a substituent group(s). Suitable substituent groups include alkyl groups such as methyl, ethyl, (iso)propyl and hexyl, alkoxy groups such as methoxy, ethoxy and (iso)propoxy, halogen atoms such as fluorine, chlorine, bromine and iodine, cyano groups, amino groups, aromatic hydrocarbon groups, ester groups, ether groups, acyl groups, and thioether groups, and a mixture thereof. No particular limits are imposed on the position at which the substituent group is attached and the number of substituent groups. Typical examples of the nitrogen-containing heterocycle include piperidine, piperazine, morpholine, pyrrolidine, pyrrolidone, piperidone and derivatives thereof.

$R^3$ is a divalent hydrocarbon group of 1 to 10 carbon atoms, preferably 1 to 6 carbon atoms. Suitable divalent hydrocarbon groups include alkylene groups such as methylene, ethylene, methylethylene, propylene, methylpropylene, tetramethylene, hexamethylene, octamethylene, decamethylene, and isobutylene, arylene groups such as phenylene, and aralkylene groups such as methylenephenylene and methylenephenylenemethylene.

Examples of the nitrogen-containing organoxysilane compound having formula (1) include:
3-dimethylaminopropyltrimethoxysilane,
3-dimethylaminopropylmethyldimethoxysilane,
3-dimethylaminopropyldimethylmethoxysilane,
3-dimethylaminopropyltriethoxysilane,
3-dimethylaminopropylmethyldiethoxysilane,
3-dimethylaminopropyldimethylethoxysilane,
3-diethylaminopropyltrimethoxysilane,
3-diethylaminopropylmethyldimethoxysilane,
3-diethylaminopropyldimethylmethoxysilane,
3-diethylaminopropyltriethoxysilane,
3-diethylaminopropylmethyldiethoxysilane, 3-diethylaminopropyldimethylethoxysilane,
3-dipropylaminopropyltrimethoxysilane,
3-dipropylaminopropylmethyldimethoxysilane,
3-dipropylaminopropyldimethylmethoxysilane,
3-dipropylaminopropyltriethoxysilane,
3-dipropylaminopropylmethyldiethoxysilane,
3-dipropylaminopropyldimethylethoxysilane,
3-dibutylaminopropyltrimethoxysilane,
3-dibutylaminopropylmethyldimethoxysilane,
3-dibutylaminopropyldimethylmethoxysilane,
3-dibutylaminopropyltriethoxysilane,
3-dibutylaminopropylmethyldiethoxysilane,
3-dibutylaminopropyldimethylethoxysilane,
3-phenylmethylaminopropyltrimethoxysilane,
3-phenylmethylaminopropylmethyldimethoxysilane,
3-phenylmethylaminopropyldimethylmethoxysilane,
3-phenylmethylaminopropyltriethoxysilane,
3-phenylmethylaminopropylmethyldiethoxysilane,
3-phenylmethylaminopropyldimethylethoxysilane,
3-piperidinylpropyltrimethoxysilane,
3-piperidinylpropylmethyldimethoxysilane,
3-piperidinylpropyldimethylmethoxysilane,
3-piperidinylpropyltriethoxysilane,
3-piperidinylpropylmethyldiethoxysilane,
3-piperidinylpropyldimethylethoxysilane,
3-morpholinylpropyltrimethoxysilane,
3-morpholinylpropylmethyldimethoxysilane,
3-morpholinylpropyldimethylmethoxysilane,
3-morpholinylpropyltriethoxysilane,
3-morpholinylpropylmethyldiethoxysilane,
3-morpholinylpropyldimethylethoxysilane,
3-(4-methylpiperadin-1-yl)propyltrimethoxysilane,
3-(4-methylpiperadin-1-yl)propylmethyldimethoxysilane,
3-(4-methylpiperadin-1-yl)propyldimethylmethoxysilane,
3-(4-methylpiperadin-1-yl)propyltriethoxysilane,
3-(4-methylpiperadin-1-yl)propylmethyldiethoxysilane,
3-(4-methylpiperadin-1-yl)propyldimethylethoxysilane, etc.

The nitrogen-containing organoxysilane compound having formula (2) is isomeric to the nitrogen-containing organoxysilane compound having formula (1). Examples of the nitrogen-containing organoxysilane compound having formula (2) include:
2-dimethylaminopropyltrimethoxysilane,
2-dimethylaminopropylmethyldimethoxysilane,
2-dimethylaminopropyldimethylmethoxysilane,
2-dimethylaminopropyltriethoxysilane,
2-dimethylaminopropylmethyldiethoxysilane,
2-dimethylaminopropyldimethylethoxysilane,
2-diethylaminopropyltrimethoxysilane,
2-diethylaminopropylmethyldimethoxysilane,
2-diethylaminopropyldimethylmethoxysilane,
2-diethylaminopropyltriethoxysilane,
2-diethylaminopropylmethyldiethoxysilane,
2-diethylaminopropyldimethylethoxysilane,
2-dipropylaminopropyltrimethoxysilane,
2-dipropylaminopropylmethyldimethoxysilane,
2-dipropylaminopropyldimethylmethoxysilane,
2-dipropylaminopropyltriethoxysilane,
2-dipropylaminopropylmethyldiethoxysilane,
2-dipropylaminopropyldimethylethoxysilane,
2-dibutylaminopropyltrimethoxysilane,
2-dibutylaminopropylmethyldimethoxysilane,
2-dibutylaminopropyldimethylmethoxysilane,
2-dibutylaminopropyltriethoxysilane,
2-dibutylaminopropylmethyldiethoxysilane,
2-dibutylaminopropyldimethylethoxysilane,
2-phenylmethylaminopropyltrimethoxysilane,
2-phenylmethylaminopropylmethyldimethoxysilane,
2-phenylmethylaminopropyldimethylmethoxysilane,
2-phenylmethylaminopropyltriethoxysilane,
2-phenylmethylaminopropylmethyldiethoxysilane,
2-phenylmethylaminopropyldimethylethoxysilane,
2-piperidinylpropyltrimethoxysilane,
2-piperidinylpropylmethyldimethoxysilane,
2-piperidinylpropyldimethylmethoxysilane,
2-piperidinylpropyltriethoxysilane,
2-piperidinylpropylmethyldiethoxysilane,
2-piperidinylpropyldimethylethoxysilane,
2-morpholinylpropyltrimethoxysilane,
2-morpholinylpropylmethyldimethoxysilane,
2-morpholinylpropyldimethylmethoxysilane,
2-morpholinylpropyltriethoxysilane,
2-morpholinylpropylmethyldiethoxysilane,
2-morpholinylpropyldimethylethoxysilane,
2-(4-methylpiperadin-1-yl)propyltrimethoxysilane,
2-(4-methylpiperadin-1-yl)propylmethyldimethoxysilane,
2-(4-methylpiperadin-1-yl)propyldimethylmethoxysilane,
2-(4-methylpiperadin-1-yl)propyltriethoxysilane,
2-(4-methylpiperadin-1-yl)propylmethyldiethoxysilane,
2-(4-methylpiperadin-1-yl)propyldimethylethoxysilane, etc.

With respect to the compositional ratio of the nitrogen-containing organoxysilane compound having formula (1) to the nitrogen-containing organoxysilane compound having formula (2), the composition consists essentially of 90 to 99 parts by weight of the compound of formula (1) and 1 to 10 parts by weight of the compound of formula (2), preferably 90 to 95 parts by weight of the compound of formula (1) and 5 to 10 parts by weight of the compound of formula (2).

Another embodiment of the invention is a method for preparing the composition containing nitrogen-containing organoxysilane compound, comprising the step of hydrosilylating an unsaturated bond-bearing nitrogen compound having the general formula (3):

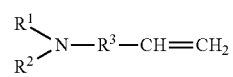

(3)

wherein $R^1$, $R^2$, and $R^3$ are as defined above and a hydrogenorganoxysilane compound having the general formula (4):

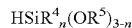

(4)

wherein $R^4$, $R^5$, and n are as defined above in the presence of an inorganic acid ammonium salt and a platinum catalyst.

Examples of the unsaturated bond-bearing nitrogen compound having formula (3) include dimethylallylamine, diethylallylamine, dipropylallylamine, dibutylallylamine, phenylmethylallylamine, N-allylpiperidine, N-allylmorpholine, and 1-allyl-4-methylpiperazine.

Examples of the hydrogenorganoxysilane compound having formula (4) include trimethoxysilane, methyldimethoxysilane, dimethylmethoxysilane, triethoxysilane, methyldiethoxysilane, and dimethylethoxysilane.

On reaction, the unsaturated bond-bearing nitrogen compound having formula (3) and the hydrogenorganoxysilane compound having formula (4) may be combined in any desired ratio. It is preferred from the aspects of reactivity and productivity to use 0.1 to 4 moles, more preferably 0.2 to 2 moles of the compound having formula (4) per mole of the compound having formula (3).

Examples of the inorganic acid ammonium salt used herein include ammonium chloride, ammonium sulfate, ammonium hydrogensulfate, ammonium nitrate, ammonium dihydrogenphosphate, diammonium hydrogenphosphate, ammonium phosphate, ammonium hypophosphite, ammonium carbonate, ammonium hydrogencarbonate, ammonium sulfide, ammonium borate, and ammonium borofluoride. From the aspects of reactivity improvement and an isomer formation controlling effect, inorganic acid ammonium salts having pKa of at least 2 are preferred, with ammonium carbonate and ammonium hydrogencarbonate being most preferred.

Although the amount of the inorganic acid ammonium salt used is not particularly limited, it is preferred from the aspects of reactivity, selectivity and productivity to use 0.00001 to 0.1 mole, especially 0.0001 to 0.05 mole of the ammonium salt per mole of the unsaturated bond-bearing compound having formula (3).

Examples of the platinum catalyst used herein include chloroplatinic acid, alcohol solutions of chloroplatinic acid, toluene or xylene solution of platinum-1,3-divinyl-1,1,3,3-tetramethyldisiloxane complex, tetrakis(triphenylphosphine)platinum, dichlorobis(triphenylphosphine)platinum, dichlorobis(acetonitrile)platinum, dichlorobis(benzonitrile)platinum, dichloro(cyclooctadiene)platinum, and platinum on active carbon.

Although the amount of the platinum catalyst used is not particularly limited, it is preferred from the aspects of reactivity and productivity to use 0.000001 to 0.01 mole, especially 0.00001 to 0.001 mole of the platinum catalyst per mole of the unsaturated bond-bearing compound having formula (3).

For the reaction, the temperature is preferably in a range of 0 to 200° C., more preferably 20 to 150° C., though not critical, and the time is preferably 1 to 40 hours, more preferably 1 to 20 hours, though not critical. The reaction atmosphere is preferably an inert gas atmosphere such as nitrogen or argon.

Although the reaction may run even in a solventless system, a solvent may be used. Suitable solvents include hydrocarbon solvents such as pentane, hexane, cyclohexane, heptane, isooctane, benzene, toluene, and xylene, ether solvents such as diethyl ether, tetrahydrofuran, and dioxane, ester solvents such as ethyl acetate and butyl acetate, aprotic polar solvents such as acetonitrile, N,N-dimethylformamide and N-methylpyrrolidone, and chlorinated hydrocarbon solvents such as dichloromethane and chloroform, which may be used alone or in admixture of two or more.

Depending on the intended application and desired quality, the composition containing nitrogen-containing organoxysilane compound resulting from the above reaction may be purified by any suitable means prior to use. Suitable purifying means include distillation, filtration, washing, column separation and solid adsorption. To obtain a high purity product by removing the catalyst and trace impurities, purification by distillation is preferred.

EXAMPLE

Examples of the invention are given below by way of illustration and not by way of limitation.

Example 1

A flask equipped with a stirrer, reflux condenser, dropping funnel and thermometer was charged with 97.9 g (1.15 mol) of dimethylallylamine, 1.5 g (45 mg of Pt) of a 3 wt % toluene solution of platinum-1,3-divinyl-1,1,3,3-tetramethyldisiloxane complex, and 1.8 g (0.023 mol) of ammonium hydrogencarbonate, and heated at 55° C. Once the internal temperature became steady, 140.6 g (1.15 mol) of trimethoxysilane was added dropwise over 7 hours, followed by stirring for 1 hour at the temperature. The reaction solution was analyzed by gas chromatography and GC-MS, finding that 3-dimethylaminopropyltrimethoxysilane and 2-dimethylaminopropyltrimethoxysilane formed in a weight ratio of 92.8:7.2. On distillation of the reaction solution, 164.5 g of a fraction having a boiling point of 78-81° C./1.0 kPa was collected. The fraction contained 92.5% by weight of 3-dimethylaminopropyltrimethoxysilane and 6.7% by weight of 2-dimethylaminopropyltrimethoxysilane.

Example 2

A flask equipped with a stirrer, reflux condenser, dropping funnel and thermometer was charged with 85.2 g (1.0 mol) of dimethylallylamine, 1.3 g (39 mg of Pt) of a 3 wt % toluene solution of platinum-1,3-divinyl-1,1,3,3-tetramethyldisiloxane complex, and 1.6 g (0.02 mol) of ammonium hydrogencarbonate, and heated at 55° C. Once the internal temperature became steady, 164.3 g (1.0 mol) of triethoxysilane was added dropwise over 9 hours, followed by stirring for 8 hours at the temperature. The reaction solution was analyzed by gas chromatography and GC-MS, finding that 3-dimethylaminopropyltriethoxysilane and 2-dimethylaminopropyltriethoxysilane formed in a weight ratio of 91.7:8.3. On distillation of the reaction solution, 180.7 g of a fraction having a boiling point of 93-96° C./1.0 kPa was collected. The fraction contained 92.3% by weight of 3-dimethylaminopropyltriethoxysilane and 6.8% by weight of 2-dimethylaminopropyltriethoxysilane.

Comparative Example 1

Reaction was conducted as in Example 1 aside from omitting ammonium hydrogencarbonate. In the reaction solution, 3-dimethylaminopropyltrimethoxysilane and 2-dimethylaminopropyltrimethoxysilane formed in a weight ratio of 63.8:36.2. On distillation of the reaction solution, 156.5 g of a fraction having a boiling point of 77-81° C./1.0 kPa was collected. The fraction contained 65.5% by weight of 3-dimethylaminopropyltrimethoxysilane and 33.5% by weight of 2-dimethylaminopropyltrimethoxysilane.

Comparative Example 2

Reaction was conducted as in Example 2 aside from omitting ammonium hydrogencarbonate. In the reaction solution, 3-dimethylaminopropyltriethoxysilane and 2-dimethylaminopropyltriethoxysilane formed in a weight ratio of 56.7:43.3. On distillation of the reaction solution, 175.4 g of a fraction having a boiling point of 92-96° C./1.0 kPa was collected. The fraction contained 57.9% by weight of 3-dimethylaminopropyltriethoxysilane and 41.1% by weight of 2-dimethylaminopropyltriethoxysilane.

Example 3

A flask equipped with a stirrer, reflux condenser, dropping funnel and thermometer was charged with 127.8 g (1.5 mol) of dimethylallylamine, 2.0 g (60 mg of Pt) of a 3 wt % toluene solution of platinum-1,3-divinyl-1,1,3,3-tetramethyldisiloxane complex, and 1.2 g (0.015 mol) of ammonium hydrogencarbonate, and heated at 45° C. Once the internal temperature became steady, 159.3 g (1.5 mol) of methyldimethoxysilane was added dropwise over 6 hours, followed by stirring for 6 hours at the temperature. The reaction solution was analyzed by gas chromatography and GC-MS, finding that 3-dimethylaminopropylmethyldimethoxysilane and 2-dimethylaminopropylmethyldimethoxysilane formed in a weight ratio of 90.7:9.3. On distillation of the reaction solution, 223.4 g of a fraction having a boiling point of 85-89° C./2.5 kPa was collected. The fraction contained 91.4% by weight of 3-dimethylaminopropylmethyldimethoxysilane and 8.0% by weight of 2-dimethylaminopropylmethyldimethoxysilane.

Comparative Example 3

Reaction was conducted as in Example 3 aside from omitting ammonium hydrogencarbonate. In the reaction solution, 3-dimethylaminopropylmethyldimethoxysilane and 2-dimethylaminopropylmethyldimethoxysilane formed in a weight ratio of 56.4:43.6. On distillation of the reaction solution, 218.8 g of a fraction having a boiling point of 84-89° C./2.5 kPa was collected. The fraction contained 58.1% by weight of 3-dimethylaminopropylmethyldimethoxysilane and 41.0% by weight of 2-dimethylaminopropylmethyldimethoxysilane.

Japanese Patent Application No. 2013-239681 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A composition containing nitrogen-containing organoxysilane compound consisting essentially of:
   90 to 95 parts by weight of a nitrogen-containing organoxysilane compound having the general formula (1):

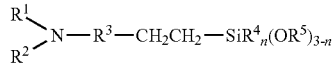
(1)

wherein $R^1$ and $R^2$ are each independently a substituted or unsubstituted, monovalent hydrocarbon group of 1 to 20 carbon atoms, or may bond together to form a ring with the nitrogen atom to which they are attached, the ring may contain a heteroatom in addition to the nitrogen atom or have a substituent group, $R^3$ is a divalent hydrocarbon group of 1 to 10 carbon atoms, $R^4$ and $R^5$ are each independently a substituted or unsubstituted, monovalent hydrocarbon group of 1 to 20 carbon atoms, n is 0, 1 or 2, and 5 to 10 parts by weight of a nitrogen-containing organoxysilane compound having the general formula (2):

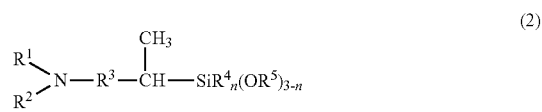
(2)

wherein $R^1$, $R^2$, $R^3$, $R^4$, $R^5$, and n are as defined above.

2. The composition of claim 1 wherein $R^1$ and $R^2$ are methyl and $R^3$ is methylene.

3. A method for preparing the composition containing nitrogen-containing organoxysilane compound of claim 1, comprising the step of hydrosilylating an unsaturated bond-bearing nitrogen compound having the general formula (3):

(3)

wherein $R^1$, $R^2$, and $R^3$ are as defined above and a hydrogenorganoxysilane compound having the general formula (4):

(4)

wherein $R^4$, $R^5$, and n are as defined above in the presence of an inorganic acid ammonium salt and a platinum catalyst.

* * * * *